(12) United States Patent
Hammer

(10) Patent No.: US 7,554,660 B2
(45) Date of Patent: Jun. 30, 2009

(54) PLASMA SPECTROSCOPY SYSTEM WITH A GAS SUPPLY

(75) Inventor: Michael Ron Hammer, Sassafras (AU)

(73) Assignee: Varian Australia Pty Ltd, Mulgrave, Victoria (AU)

( * ) Notice: Subject to any disclaimer, the term of this patent is extended or adjusted under 35 U.S.C. 154(b) by 162 days.

(21) Appl. No.: 11/887,196

(22) PCT Filed: Mar. 31, 2006

(86) PCT No.: PCT/AU2006/000423

§ 371 (c)(1),
(2), (4) Date: Sep. 26, 2007

(87) PCT Pub. No.: WO2006/102712

PCT Pub. Date: Oct. 5, 2006

(65) Prior Publication Data

US 2009/0059221 A1 Mar. 5, 2009

(30) Foreign Application Priority Data

Mar. 31, 2005 (AU) .............................. 2005901575

(51) Int. Cl.
*G01N 21/73* (2006.01)
(52) U.S. Cl. .................................................... 356/316
(58) Field of Classification Search ................... 356/316
See application file for complete search history.

(56) References Cited

FOREIGN PATENT DOCUMENTS

| EP | 0296002 | 12/1998 |
|----|---------|---------|
| GB | 1049240 | 11/1966 |
| JP | 06-203790 | 7/1994 |

OTHER PUBLICATIONS

Palmieri et al., Determination of methylmercury in fish tissue by gas chromatography with microwave-induced plasma atomic emission spectrometry after derivatization with sodium tetraphenylborate, Fresenius' Journal of Analytical Chemistry, vol. 366, No. 5, Mar. 2000, pp. 466-469.*

* cited by examiner

*Primary Examiner*—F. L Evans
(74) *Attorney, Agent, or Firm*—Bella Fishman

(57) ABSTRACT

A spectroscopy system for spectro-chemical analysis of a sample includes a plasma torch (50) for generating a microwave induced plasma (90) as a spectroscopic source. The plasma forming gas is nitrogen which can contain an oxygen impurity. Thus the system includes a nitrogen generator (70) which is preferably supplied with compressed atmospheric air from a compressor (75) for oxygen to be removed from the air by adsorption. The invention allows the use of an on-site nitrogen gas generator and thus gives cost savings because the need to obtain supplies of bottled high purity gas is eliminated.

10 Claims, 2 Drawing Sheets

PLASMA SPECTROSCOPY SYSTEM WITH A GAS SUPPLY

TECHNICAL FIELD

The present invention relates to a spectroscopy system having a gas supply for sustaining a plasma as a part of the system. The system is for spectro chemical elemental analysis of a sample.

BACKGROUND

The following discussion of the background to the invention is included to explain the context of the invention. This is not to be taken as an admission that any of the material referred to was, in Australia, published, known or part of the common general knowledge as at the priority date established by the present application.

All spectroscopic based elemental analysers (except those that use X-ray techniques) require a gas supply, for example acetylene and nitrous oxide for flame atomic absorption spectroscopy (FAAS), or argon for inductively coupled plasma (ICP) emission or mass spectrometry. For a microwave induced plasma spectroscopic source, a preferred plasma forming gas is nitrogen, as disclosed in the applicant's International application No. PCT/AU01/00805 (WO 02/04930 A1) at pages 9-10 (which has been granted as U.S. Pat. No. 6,683,272 B2).

Providing a gas supply for spectroscopy systems is typically very expensive, for example the annual gas supply costs can amount to as much as the initial purchase price of a spectroscopy instrument and possibly be even higher if the gas has to be supplied to a remote location. A significant factor in this cost is the high purity customarily required of the supplied gas. For example, commercially supplied nitrogen is typically specified as containing less than 0.1% by volume of oxygen and argon together.

DISCLOSURE OF THE INVENTION

The present invention provides a spectroscopy system including a torch for generating a microwave induced plasma as a spectroscopic source, a generator for generating a supply of nitrogen gas, the generator being connected to the torch for supplying the nitrogen gas for sustaining the plasma, wherein the generator generates the nitrogen gas from atmospheric air.

A microwave induced plasma source for spectroscopy can operate satisfactorily, and in certain conditions give improved performance for the spectroscopy system, on substantially nitrogen which contains some oxygen as the plasma sustaining gas. This means that the gas supply can be provided by a nitrogen generator located at the site of the spectroscopy instrument for which the gas input is atmospheric air (that is, the air at the location of the generator). For example, it is possible to create a nitrogen enriched gas supply from atmospheric air that is compressed at the location of the spectroscopy instrument by use of a gas-selective filtration membrane, or by pressure-swing adsorption of oxygen by use of a suitable sorbent such as a carbon molecular sieve. Such a generator can supply nitrogen containing typically between 0.1% and 5% by volume residual oxygen and only small or trace amounts of the rarer atmospheric gases such as argon, $CO_2$ etc. A microwave induced plasma spectroscopy system according to the invention can operate satisfactory on such a nitrogen supply.

Thus the invention allows for the use of an on-site nitrogen gas generator and this gives significant cost savings because the need to obtain supplies of bottled high purity gas is eliminated as is the cost of transportation of the bottled gas supplies to the location of the spectroscopy instrument. In remote locations, at sites where access is difficult, or in countries with a low level of infrastructure, the cost savings could be so large as to make the difference between being able to operate the spectroscopy instrument and not being able to operate it.

Preferably the generated nitrogen for the invention contains between about 0.1% to about 3.0% by volume of oxygen. More preferably the nitrogen contains between about 0.1% to about 2.0% by volume of oxygen. Even more preferably the nitrogen contains between about 0.5% to 1.5% by volume of oxygen.

It is thought that an improved sensitivity of a spectroscopy system according to the invention increases from an oxygen content of the nitrogen of about 0.1% by volume and is maximised when the nitrogen contains between about 1% to 2% by volume of oxygen and then decreases for concentrations greater than about 2% by volume of oxygen. Further experiments are being conducted to determine these ranges for the oxygen content.

Preferably the generator of the invention is one which operates by adsorption of oxygen from an air supply.

For a better understanding of the invention and to show how the same may be performed, a preferred embodiment thereof will now be disclosed by way of non-limiting example only, with reference to the accompanying drawings.

DETAILED DESCRIPTION

Tests were undertaken to determine the sensitivity of a microwave induced plasma spectrochemical system to nitrogen purity. These tests measured the signal level in A/D counts received in 1 second for a 1 mg/L solution of the element of interest. Representative results are shown in the tables below. The spectroscopy instrument was optimised differently for the two sets of data, but the set-up was unchanged within each set of results.

| Element | Counts with pure nitrogen (from evaporation of liquid nitrogen) | Counts with oxygen-depleted air (principally nitrogen with ~1.5% oxygen) |
| --- | --- | --- |
| Aluminium | 105492 | 103315 |
| Arsenic | 7665 | 12570 |
| Cadmium | 68427 | 88959 |
| Cobalt | 23636 | 38009 |
| Chromium | 74641 | 75860 |
| Copper | 221123 | 342675 |
| Manganese | 58920 | 75524 |
| Molybdenum | 74310 | 79514 |
| Nickel | 47786 | 70486 |
| Lead | 11160 | 13039 |
| Strontium | 1352067 | 1447932 |
| Zinc | 36386 | 51618 |

| Element | Counts with pure nitrogen (from evaporation of liquid nitrogen) | Counts with oxygen-depleted air (principally nitrogen with ~2.5% oxygen) |
| --- | --- | --- |
| Aluminium | 97125 | 125676 |
| Arsenic | 28513 | 21716 |
| Cadmium | 174468 | 195209 |
| Cobalt | 15028 | 35807 |
| Chromium | 65815 | 66955 |
| Copper | 139458 | 353904 |
| Manganese | 116046 | 99425 |
| Molybdenum | 36292 | 70762 |
| Nickel | 26250 | 63983 |
| Lead | 12688 | 11772 |
| Strontium | 1249902 | 945604 |
| Zinc | 94081 | 93208 |

As the results in the above two tables show, a small amount of residual oxygen (up to 2-3%) in the gas supplied to the plasma is beneficial and actually improves the sensitivity. This improvement is also reflected in the detection limits obtainable. These improvements may be modest, but they are certainly worthwhile.

Figure 1:
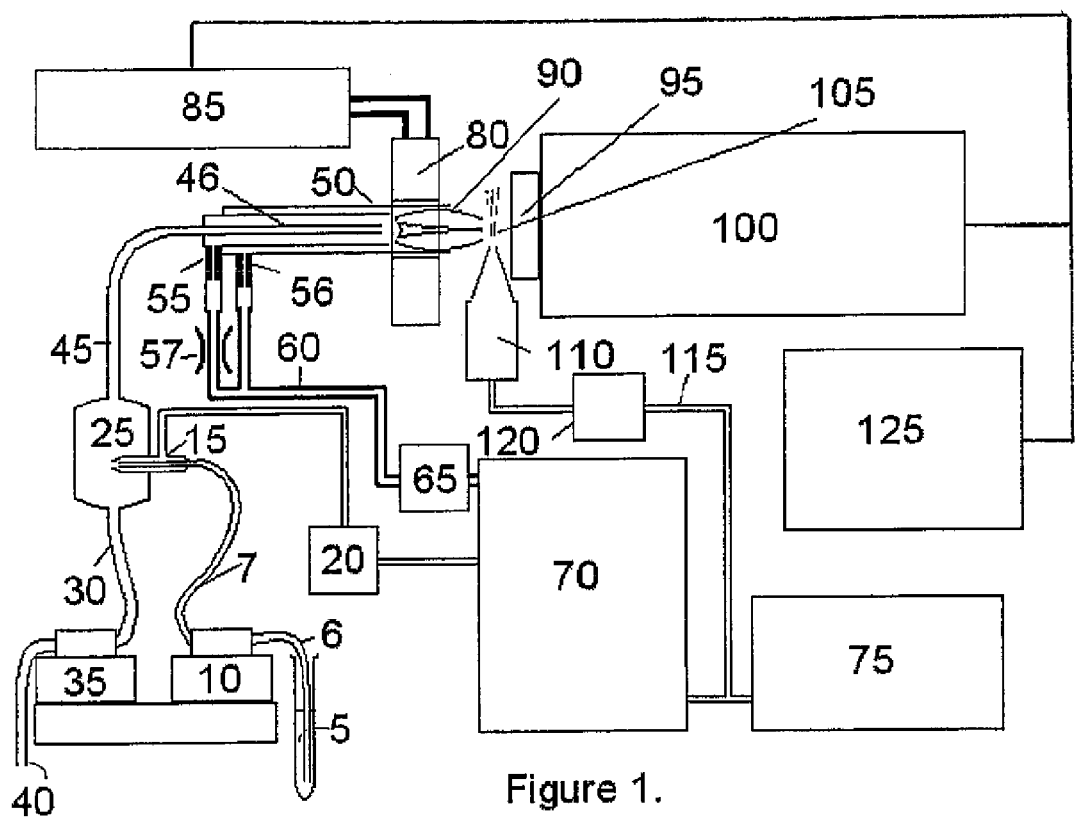
FIG. 1 schematically illustrates a spectroscopy system according to an embodiment of the invention.

In the spectroscopy system schematically illustrated by FIG. 1, a representative portion of a liquid analytical sample 5 is pumped through a probe 6 to sample transfer tube 7 by a pump 10 and passes into an aerosol generating device 15. Many suitable aerosol generating devices are known in the art. In the example shown the aerosol generating device 15 is a pneumatic nebulizer supplied with nitrogen at an appropriate pressure (50-500 kPa gauge, typically 120-250 kPa gauge) controlled by a pressure regulator 20. Aerosol generating device 15 converts the liquid taken as described from analytical sample 5 into an aerosol (not shown) in a spray chamber 25 within which larger aerosol droplets settle out and are drained away through a drain tube 30 by a second pump 35 to a waste outlet 40. The aerosol consisting of fine droplets suspended in nitrogen passes through an aerosol transfer tube 45 to an injector tube 46 of a plasma torch 50.

The above described arrangement illustrates merely a preferred way in which an analytical sample can be converted into a form suitable for introduction into a plasma torch for spectrochemical analysis. Many other arrangements are known in the art and are widely used in conjunction with other types of spectrochemical plasmas, such as the inductively coupled plasma. Any such sample introduction arrangements may be substituted for the arrangement just described.

Plasma torch 50 is supplied with two gas flows through inlets 55 and 56 from a manifold 60. The flow required through inlet 55 is less than that required through inlet 56. A restrictor 57 is placed between inlet 55 and manifold 60 to achieve the required flow. A pressure regulator 65 provides constant gas pressure in manifold 60. Details of torches suitable for microwave induced plasmas that may be used for torch 50 are described in the applicant's International applications Nos. PCT/AU01/00805 (WO 02/04930 A1—at pp 11-12) and PCT/AU03/00615 (WO 03/098980 A1).

According to an embodiment of the invention nitrogen is supplied to manifold 60 and to pressure regulators 20 and 65 from a nitrogen generator 70, which is supplied with compressed atmospheric air from an air compressor 75.

Plasma torch 50 is located in a microwave cavity 80, which is provided with microwave power by a microwave power supply 85. A plasma 90 is generated in torch 50 by the action of microwaves in the microwave cavity 80. Details of cavity 80 and its use to generate a nitrogen plasma for spectrochemical analysis are described in the above mentioned U.S. Pat. No. 6,683,272 B2 and in the applicant's International application No. PCT/AU02/01142 (WO 03/069964 A1).

The plasma 90 is viewed through an optical interface 95 by an optical spectrometer 100 for spectrochemical analysis. Optical interface 95 is protected from plasma 90 by an air curtain 105 generated by passing air through a nozzle arrangement 110. Air is provided to the nozzle arrangement 110 from an air compressor 75 via an air line 115. A pressure regulator 120 is provided in line 115 to provide an appropriate flow of air through the nozzle arrangement 110.

The optical interface 95 and optical spectrometer 100 can be replaced by any one of several types of mass spectrometer as known in the art, and in such circumstances an air curtain 105 is not required. Details of interfacing a plasma to a mass spectrometer for spectrochemical analysis are known in the art.

An electronic control and data processing system 125 is provided to control the operation of the system and to collect and process the data generated by spectrometer 100.

Figure 2:
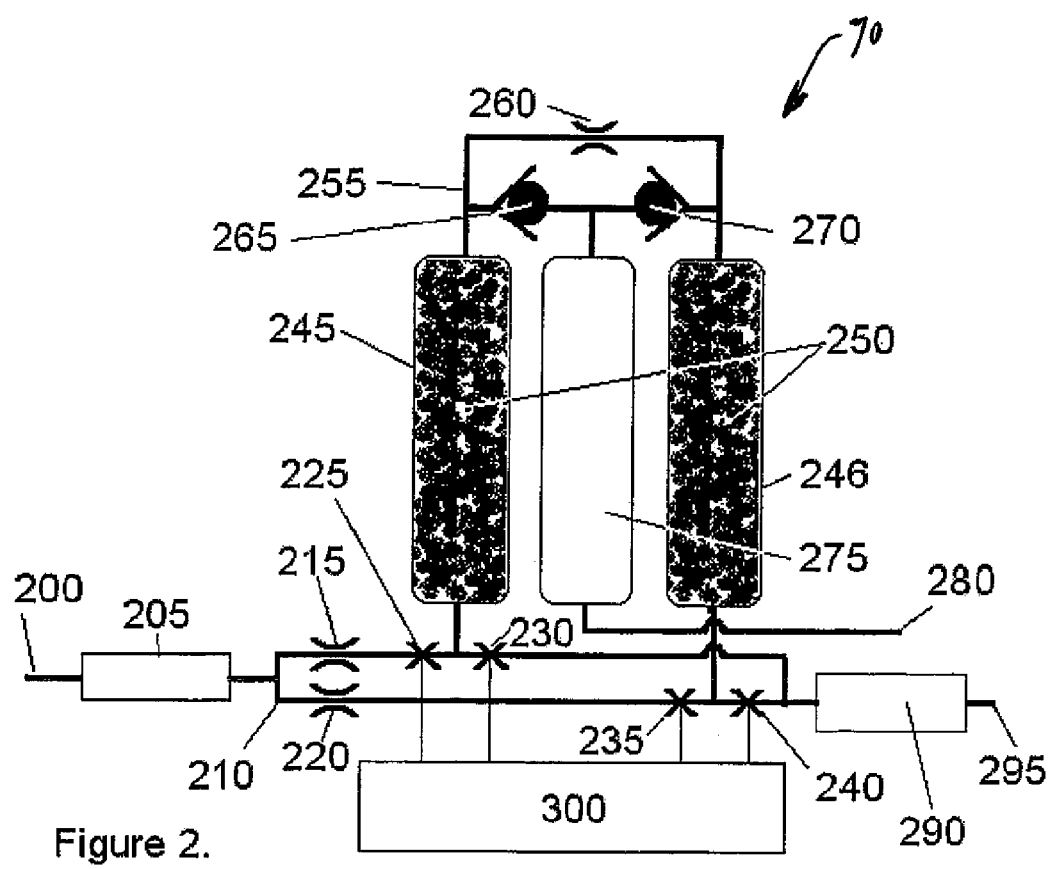
FIG. 2 schematically illustrates a nitrogen generator for use in the system of FIG. 1.

An embodiment of a nitrogen generator 70 is schematically illustrated by FIG. 2. In this generator 70, atmospheric air from an air compressor (not shown) passes through an air filter 205 into a first manifold 210 provided with flow restrictors 215 and 220 and solenoid valves 225, 230, 235 and 240.

Flow restrictors 215 and 220 can be implemented as a single flow restrictor (not shown) between filter 205 and manifold 210. For simplicity of exposition of the operation of the apparatus it will be assumed that the flow is controlled by solenoid valves 225, 230, 235 and 240 as shown in FIG. 2, but it is to be understood that the set of individual valves 225, 230, 235 and 240 can be replaced by any appropriate set of valves providing the same functionality as known to those skilled in the art.

Initially solenoid valve 225 is open, solenoid valve 230 is closed, solenoid valve 235 is closed and solenoid valve 240 is open. The switching of solenoid valves 225, 230, 235 and 240 is carried out by an electronic control device 300. Air from the first manifold 210 flows through valve 225 into a first pressure vessel 245, having a volume of for example 11 liters, which is packed with an appropriate adsorbent medium 250, such as a carbon molecular sieve. A suitable carbon molecular sieve is CMS-190 manufactured by the China Yancheng Baode Chemical Co Ltd, Baota Town, Yancheng, Jiangsu, China. As air flows at high pressure (~530 kPa) over the adsorbent medium 250 in pressure vessel 245 oxygen is selectively adsorbed by adsorbent medium 250 and the air is progressively depleted of oxygen. The air depleted of oxygen passes from pressure vessel 245 into a second manifold 255. A small fraction of the air in the second manifold 255 passes through a flow restrictor 260 into a second pressure vessel 246 having a volume of, for example, 11 liters, that is also packed with adsorbent material 250. The second pressure vessel 246 is vented to atmosphere through a waste outlet 295 via the open solenoid valve 240, so the pressure in the second pressure vessel 246 is much lower than that in the first pressure vessel 245. On its way through the second pressure vessel 246 air from the flow restrictor 260 sweeps adsorbed oxygen from the adsorbent medium 250 and passes through solenoid valve 240 to a muffler 290 and exits through the waste outlet 295. The major portion of oxygen-depleted air from the second manifold 255 passes through a first one-way valve 265 into a nitrogen reservoir 275.

After a pre-determined period of time (typically one minute) the states of solenoid valves 225, 230, 235 and 240 are switched by electronic control device 300 so that solenoid valve 225 is closed, solenoid valve 230 is open, solenoid valve 235 is open and solenoid valve 240 is closed. The air from the first manifold 210 now flows at high pressure (~530 kPa) through the valve 235 into the second pressure vessel 246. As air flows at high pressure over the adsorbent medium 250 in the second pressure vessel 246 oxygen is selectively adsorbed by adsorbent medium 250 and the air is progressively depleted of oxygen. The air depleted of oxygen passes from the second pressure vessel 246 into the second manifold 255. A small fraction of the air in the second manifold 255 passes through the flow restrictor 260 into the first pressure vessel 245. The pressure in the first pressure vessel 245 is now much lower than that in second pressure vessel 246 because valve 230 is open to the waste outlet 295. On its way through first pressure vessel 245 air from flow restrictor 260 sweeps adsorbed oxygen from the adsorbent medium 250 in the first pressure vessel 245 and passes through solenoid valve 230 to muffler 290 and exits through the waste outlet 295. The major portion of oxygen-depleted air from the second manifold 255 passes through a second one-way valve 270 into the nitrogen reservoir 275.

After a pre-determined period of time (typically one minute) the states of solenoid valves 225, 230, 235, and 240 are switched again by electronic control device 300 and the cycle repeats. After several cycles the oxygen-depleted air in the nitrogen reservoir 275 contains less than about 5% by vol oxygen and consists predominantly of nitrogen. This gas can be withdrawn through an outlet 280 via appropriate gas pressure regulating and flow control means (not shown).

The invention described herein is susceptible to variations, modifications and/or additions other than those specifically described and it is to be understood that the invention includes all such variations, modifications and/or additions which fall within the scope of the following claims.

The invention claimed is:

1. A spectroscopy system including a torch for generating a microwave induced plasma as a spectroscopic source, a generator for generating a supply of nitrogen gas, the generator being connected to the torch for supplying the nitrogen gas for sustaining the plasma, wherein the generator generates the nitrogen gas from atmospheric air.

2. A spectroscopy system as claimed in claim 1 wherein the generator operates by adsorption of oxygen from atmospheric air.

3. A spectroscopy system as claimed in claim 1 including an air compressor for supplying compressed atmospheric air to the generator.

4. A spectroscopy system as claimed in claim 3 wherein the generator includes a first pressure vessel containing an oxygen adsorbent medium through which the compressed atmospheric air is passed.

5. A spectroscopy system as claimed in claim 4 including another pressure vessel into which the oxygen depleted and thus nitrogen rich air passes from the first pressure vessel, and wherein the nitrogen gas for sustaining the plasma is supplied from said another pressure vessel.

6. A spectroscopy system as claimed in claim 5 wherein the generator includes a second pressure vessel containing an oxygen adsorbent medium, and wherein the generator includes flow control valves whereby the compressed atmospheric air is first passed for a predetermined period through the oxygen adsorbent medium in the first pressure vessel and then into said another pressure vessel, and then passed for a predetermined period through the oxygen adsorbent medium in the second pressure vessel and then into said another pressure vessel.

7. A spectroscopy system as claimed in claim 6 wherein the flow control valves are operable such that whilst the compressed air is being passed through the oxygen adsorbent medium in the first pressure vessel, the oxygen adsorbent medium in the second pressure vessel is purged of its adsorbed oxygen, and whilst the compressed air is being passed through the oxygen adsorbent medium in the second pressure vessel, the oxygen adsorbent medium in the first pressure vessel is purged of its adsorbed oxygen.

8. A spectroscopy system as claimed in claim 1 wherein the nitrogen gas supplied to the torch from the generator contains between about 0.1% to about 3.0% by volume of oxygen.

9. A spectroscopy system as claimed in claim 8 wherein the nitrogen contains between about 0.1% to about 2.0% by volume of oxygen.

10. A spectroscopy system as claimed in claim 9 wherein the nitrogen contains between about 0.5% to about 1.5% by volume of oxygen.

* * * * *